United States Patent [19]

Krabetz et al.

[11] 4,409,128
[45] Oct. 11, 1983

[54] OXIDATION CATALYST, ESPECIALLY FOR THE PREPARATION OF METHACRYLIC ACID BY GAS PHASE OXIDATION OF METHACROLEIN

[75] Inventors: Richard Krabetz, Kirchheim; Franz Merger, Frankenthal; Matthias Schwarzmann, Limburgerhof, all of Fed. Rep. of Germany

[73] Assignee: BASF Aktiengesellschaft, Rheinland-Pfalz, Fed. Rep. of Germany

[21] Appl. No.: 283,633

[22] Filed: Jul. 15, 1981

[30] Foreign Application Priority Data

Aug. 9, 1980 [DE] Fed. Rep. of Germany ....... 3030243

[51] Int. Cl.³ .............................................. B01J 27/14
[52] U.S. Cl. ..................................... 502/211; 502/213
[58] Field of Search ............................... 252/435, 437

[56] References Cited

U.S. PATENT DOCUMENTS

| | | | |
|---|---|---|---|
| 4,049,574 | 9/1977 | Ken et al. | 252/437 |
| 4,075,124 | 2/1978 | White et al. | 252/437 |
| 4,202,826 | 5/1980 | Ken | 260/346.75 |
| 4,273,676 | 6/1981 | Matsumoto et al. | 252/435 |
| 4,280,928 | 7/1981 | Kirch et al. | 252/435 X |
| 4,301,031 | 11/1981 | Shaw et al. | 252/437 X |
| 4,320,227 | 3/1982 | Matsumoto et al. | 252/435 X |

FOREIGN PATENT DOCUMENTS

| | | |
|---|---|---|
| 5769 | 12/1979 | European Pat. Off. . |
| 52-122317 | 10/1977 | Japan . |
| 52-68122 | 12/1977 | Japan . |
| 1473035 | 5/1977 | United Kingdom ............. 252/467 |
| 2001255 | 12/1979 | United Kingdom ............. 252/435 |
| 2040717 | 9/1980 | United Kingdom ............. 252/467 |

OTHER PUBLICATIONS

Japanese Patent Publication 68122/1977, Unsaturated Carboxylic Acid Prepn. by Oxidising (meth) Acrolein—Using Complex Catalyst Contg. Phosphorus, Molybdenum, Oxygen and e.g. Potassium, Vanadium and Iron.
Japanese Patent Publication 122317/1977, (Meth)acrylic Acid Prepn. by Catalytic Oxidn. of (meth)acrolein—Using Catalyst Contg. Molybdenum, Rhodium, Phosphorus and Oxygen.

*Primary Examiner*—Delbert E. Gantz
*Assistant Examiner*—William G. Wright
*Attorney, Agent, or Firm*—Oblon, Fisher, Spivak, McClelland & Maier

[57] ABSTRACT

An oxidation catalyst wherein the catalytically active component has the general formula $$Mo_{12}P_aRh_bCu_cV_dCs_eX_fY_gZ_hO_x,$$

where X is Cr and/or Fe, Y is Nb, Z is Na, Li, K and/or Rb, a is 0.1–4, b is 0.001–1, c is 0.05–2, d is 0.05–4, e is 0.1–5, f is 0–2, g is 0–3 and h is 0–2, and x is the number of oxygen atoms required to saturate the valencies of the other constituents, is very suitable for the preparation of methacrylic acid by gas phase oxidation of methacrolein with an oxygen-containing and steam-containing gas mixture.

1 Claim, No Drawings

OXIDATION CATALYST, ESPECIALLY FOR THE PREPARATION OF METHACRYLIC ACID BY GAS PHASE OXIDATION OF METHACROLEIN

It is known that methacrolein can be oxidized in the gas phase, with oxygen-containing gases, to give methacrylic acid. Catalysts which have been proposed are mixtures or compounds of metal oxides, which in addition to molybdenum, phosphorus and alkali metals or thallium also contain other metals. For example, Japanese published patent No. 68,122/1977 discloses catalysts which additionally contain niobium or vanadium and one or more elements from the group comprising Mn, Sb, V, Fe, Cu, Ni and Si. However, these catalysts require bath temperatures of above 330° C. and accordingly have a very short life.

Japanese Published Pat. No. 122,317/1977 proposes catalysts in which the additional elements are rhodium, metals of the group comprising V, Cr and Fe, and metals of the group comprising Se, Ti, Sn, W, Al and Th. It is true that these catalysts initially, and for a short time, give selectivities of 87.7 mole % at bath temperatures below 300° C. However, it has been found that when the catalytic material is molded, as is necessary for industrial use, the selectivity and activity diminish, and that the catalyst is sensitive to fluctuations in operating conditions, so that its life, especially at conversions above 70 mole %, is unsatisfactory.

A particular disadvantage of the catalyst systems hitherto disclosed is that their efficiency decreases greatly if technical-grade methacrolein is employed, which has been prepared by condensing propionaldehyde with formaldehyde or aminals and which contains low concentrations of such impurities as organic amines, dimers of methacrolein and methylpentenal.

We have found that the oxidation of methacrolein in the gas phase, with an oxygen-containing gas, to give methacrylic acid can be carried out advantageously by employing a catalyst whose composition may be represented by the formula

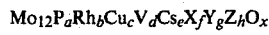

$Mo_{12}P_aRh_bCu_cV_dCs_eX_fY_gZ_hO_x$ where X is Cr and/or Fe, Y is Nb, Z is Na, Li, K and/or Rb, a is 0.1-4, preferably 0.5-3, b is 0.001-1, preferably 0.02-0.5, c is 0.05-2, preferably 0.1-1, d is 0.05-4, preferably 0.1-3, e is 0.1-5, preferably 0.5-3, f is 0-2, preferably 0.01-2 if c is 0.5, g is 0-3, preferably 0.1-2, h is 0-2 and x is the number of oxygen atoms required to saturate the valencies of the other constituents.

The catalysts according to the invention are particularly suitable for the conversion of methacrolein which has been obtained by condensing propionaldehyde with formaldehyde or aminals, since they are relatively insensitive to impurities in the methacrolein, such as amines, dimers of methacrolein and methylpentenal. Even with technical-grade methacrolein, the catalysts give selectivities of from 80 to 90 mole %, coupled with conversions of more than 60 mole %, at reaction temperatures below 330° C., and even after operating times of more than 1,000 hours no decrease in activity is observed.

A further advantage of the catalysts according to the invention is the good moldability of the catalytic material, without significant adverse effect on the catalytic properties. In some cases, the molding of the catalytic material even improves the catalytic properties. Various methods can be used to prepare the novel catalysts, mold them and, where appropriate, apply them to a carrier. A simple method of preparation is to mix the salts or oxides of the components in aqueous solution or suspension, dry the mixture at from 70° to 130° C. and then calcine it at from 180° to 600° C. A method which can be of advantage and is therefore preferred is to convert the salts, where these are used, to the oxides at a relatively low temperature, for example at 220°-340° C., and then thermally activate the oxides at from 350° to 600° C., preferably from 360° to 500° C. The calcination is preferably carried out in the absence of a stream of gas and/or in the presence of gaseous ammonia. The catalyst can be employed with or without a conventional carrier, such as silica, $Al_2O_3$, metal silicates, $TiO_2$, $ZrO_2$ or pumice.

The catalytic material can be molded before or after the activating calcination. If it is molded by tableting, it is advantageous to add a lubricant, for example graphite powder, in amounts of, in general, from 1 to 5% by weight; moistening (which tends to be detrimental) of the powder to be tableted is in general not necessary. The catalytic material can also be molded to form balls by feeding the catalyst powder and a liquid binder, in a certain ratio, in a conventional manner onto preformed catalyst nuclei which are rolling on a granulating bowl or on a rotating inclined mixer.

A preferred method of molding is to feed the catalyst powder at a constant rate onto a pre-molded inert carrier which is agitated in a rotating vessel and is continuously moistened with a liquid, wetting binder. The preferred binder is water. Suitable carriers are spherical pre-molded $Al_2O_3$ and magnesium aluminum silicate as well as conventional ceramic materials having particle diameters of 1.5–5 mm. The amount of active material on the carrier is in general 20–250% by weight, preferably 50–200% by weight, based on weight of carrier.

The process according to the invention is in general carried out under a pressure of from 1 to 5 bar and at from 200° to 400° C., advantageously from 250° to 330° C. The residence time is from 0.5 to 10 seconds, advantageously from 1 to 6 seconds. The oxidizing agent employed is generally air, but the oxygen can also be fed to the reactor in other forms, for example as pure oxygen. The oxidation is advantageously carried out in the presence of an inert gas, especially steam. The steam can in part be replaced by the off-gas from the reaction, which, after washing out and/or condensing the products, is recycled to the synthesis, in general consists of unconverted oxygen, nitrogen, carbon oxides and unconverted methacrolein and, according to the separation conditions used, may be saturated with steam. The molar ratio of methacrolein:$O_2$:$H_2O$:inert gases is in general 1:1–6:1–20:4–50, preferably 1:1.5–4:2–10:6–30.

The methacrolein employed may have been prepared by various methods, for example by gas phase oxidation of tert.-butyl alcohol, isobutylene or C4-mixtures, or by condensation of propionaldehyde with formaldehyde. The use of technical-grade methacrolein, which has been obtained by condensing propionaldehyde with formaldehyde in the presence of salts or secondary amines, or with aminals in the presence of acids in aqueous solution, is preferred.

Technical grades of methacrolein in general are 94–98% pure and contain, in addition to unconverted propionaldehyde, small amounts of organic amines, such as diethylamine or diethanolamine, methylpentenal and dimers of methacrolein. If the unconverted methacrolein is recycled, the synthesis gas mixtures can also contain small amounts of more volatile by-products from the process according to the invention. The purities mentioned relate to anhydrous crude methacrolein; in general, technical-grade methacrolein contains up to 3.5% by weight of water.

The conversion of the methacrolein can be carried out in a fluidized bed reactor, but is preferably carried out over a fixed catalyst in a tube bundle reactor. To avoid local overheating, the catalyst activity can be modified so that it increases continuously, or in steps, in the direction of flow in the reaction tube. Suitable means of achieving this are, for example, diluting the molded catalyst with less active or inactive catalyst moldings or carrier moldings, or using two or more catalysts having different activities and/or selectivities.

The methacrylic acid can be isolated from the reaction gases in a conventional manner. In general, the reaction off-gas is cooled indirectly or directly, and washed with water. The methacrylic acid, with or without acetic acid, maleic acid and acrylic acid, can be extracted from the resulting aqueous solution with suitable solvents, such as methyl methacrylate, and either be fed direct to an esterification reaction with an alkanol or be separated from the extractant and the by-products by distillation. The unconverted methacrolein can be expelled from the aqueous condensate with steam and can, with or without water and volatile by-products which have not been separated off, be recycled to the synthesis.

The catalysts according to the invention also exhibit a high activity and selectively in other oxidation processes, for example the oxidation of acrolein to acrylic acid or the oxidation of substituted toluene derivatives to substituted benzaldehydes and benzoic acids.

In the Examples which follow, parts are by weight. The methacrolein employed has a purity of 95–98% by weight and contains, in addition to propionaldehyde, small amounts of secondary amines and by-products of the synthesis of methacrolein from propionaldehyde and formaldehyde.

EXAMPLE 1

A Preparation of the catalyst 212 parts of ammonium heptamolybdate containing 220 ppm of K, 22.6 parts of 85% strength phosphoric acid, 11.7 parts of ammonium metavanadate, 7.1 parts of niobium pentoxide, 39 parts of cesium nitrate, 12.08 parts of copper nitrate and 2 parts of rhodium(III) chloride hydrate are dissolved successively in 1,200 parts of water at 60° C., with stirring. The solution is concentrated on a waterbath and the residue is dried for 12 hours at 130° C. The dry material is comminuted, mixed with 2% by weight of graphite powder and molded to give 3×3 mm tablets.

100 ml of tablets are calcined for two hours in a U-shaped reaction tube of 15 mm internal diameter, which is heated at 450° C. in a salt bath, air being passed through the tube at the rate of 8 liters (S.T.P.)/h. The resulting catalyst A has the composition $Mo_{12}V_1P_{1.96}Nb_{0.53}Cs_{1.95}Cu_{0.5}Rh_{0.1}O_x$.

B Oxidation of methacrolein to methacrylic acid 85 ml of catalyst are introduced into a stainless steel tube of 15 mm internal diameter. The tube is heated at 260° C. in a salt bath and is fed with 85.2 liters (S.T.P.)/h of a gas mixture which has been preheated to the bath temperature and consists of 4% by volume of methacrolein, 65% by volume of air and 31% by volume of steam.

The bath temperature is then slowly raised to 314° C. After 200 hours, the conversion of methacrolein is 73.8 mole %, the yield of methacrylic acid is 66.5 mole % and the selectivity is 90.1 mole %. The yields of by-products are 1.7 mole % of acetic acid, about 0.1 mole % of acrylic acid, about 0.4 mole % of maleic acid, about 0.4 mole % of other by-products, such as formaldehyde, acrolein, acetone, acetaldehyde, benzaldehyde and formic acid, and 4.8 mole % of carbon oxides. If 50 ml of catalyst are employed and the bath temperature is raised to 320° C., the conversion is 60.6% and the selectivity is 88.1 mole %.

EXAMPLE 2

A catalyst B is prepared as described in Example 1, expect that no $Nb_2O_3$ is added. The reaction is then carried out at 300° C., but otherwise under the conditions described under Example 1 B, and after 240 operating hours a conversion of 80.6 mole %, a yield of methacrylic acid of 70 mole % and a methacrylic acid selectivity of 86.8 mole % are achieved.

EXAMPLE 3

A catalyst having the composition $Mo_{12}V_1P_1Cs_1Cu_{0.5}Nb_1Rh_{0.1}O_x$ is prepared by the method described in Example 1 and is tested as described in Example 1 B. At a bath temperature of 300° C., a conversion of 77.9 mole % and a selectivity of methacrylic acid formation of 81.9 mole % are achieved. At 314° C., the conversion is 88.1 mole % and the selectivity of methacrylic acid formation is 80.2 mole %.

COMPARATIVE EXPERIMENTS A TO C, FOR COMPARISON WITH

EXAMPLE 3

Catalysts are prepared as described Example 3, except that, respectively, one of the components Cu, Rh and V is omitted. The composition of the catalyst, and the test results under the conditions of Example 1 B, are summarized in Table 1 below.

TABLE 1

| Experiment | Catalyst | Bath temperature °C. | Conversion mole % | Selectivity mole % |
|---|---|---|---|---|
| a | $Mo_{12}P_1V_1Nb_1Cs_1Cu_{0.5}O_x$ | 314 | 46.1 | 68.7 |
| b | $Mo_{12}P_1V_1Nb_1Cs_1Rh_{0.1}O_x$ | 300 | 45.5 | 81.7 |
| c | $Mo_{12}P_1Nb_1Cs_1Cu_{0.5}Rh_{0.1}O_x$ | 300 | 53.9 | 80.1 |

EXAMPLE 4

212 parts of ammonium heptamolybdate containing 220 ppm of potassium, 22.6 parts of 85% strength phosphoric acid, 11.7 parts of ammonium metavanadate, 7.1 parts of niobium pentoxide, 39 parts of cesium nitrate, 12.08 parts of copper nitrate and 2 parts of rhodium(III) chloride hydrate are successively dissolved in 1,200 parts of water at 60° C., with stirring. The solution is concentrated on a waterbath and the residue is dried for 12 hours at 130° C. The dry material is heated to 450° C. in a rotary tubular furnace, under a stream of air of 8 liters (S.T.P.)/h, and is then calcined for 2 hours at 450° C. The oxide material obtained is comminuted to a particle size of less than 50 μm. 150 parts of the powder obtained are applied to 145 parts of steatite balls of 3 mm diameter by feeding the powder, at a constant rate, to the vigorously agitated carrier in a coating drum, the carrier being continuously moistened with water. After drying in the coating drum at 70° C. by means of air at 100° C., an abrasion-resistant coated catalyst is obtained.

85 liters (S.T.P.)/h of a gas mixture containing 5% by volume of methacrolein, 65% by volume of air and 30% by volume of steam are passed over 85 ml of the catalyst in a salt bath reactor, the bath being at 314° C. A conversion of 50.1 mole %, a yield of methacrylic acid of 44 mole % and a selectivity of 89.8 mole % are achieved.

EXAMPLES 5 TO 14

Catalysts containing various proportions of rhodium, copper and phosphorus are prepared by the method described in Example 1 A and tested under the conditions described in Example 1 B. The test results are shown in Table 2 below.

TABLE 2

| Example | Catalyst composition | Bath temperature °C. | Conversion mole % | Selectivity mole % |
|---|---|---|---|---|
| 5 | $Mo_{12}P_2V_1Nb_1Cs_1Cu_{0.5}Rh_{0.2}O_x$ | 318 | 58.7 | 84.2 |
| 6 | $Mo_{12}P_2V_1Nb_{0.5}Cs_1K_{0.5}Cu_{0.5}Rh_{0.1}O_x$ | 328 | 57 | 88.2 |
| 7 | $Mo_{12}P_2V_1Nb_{0.5}Cs_1Rb_1Cu_{0.5}Rh_{0.1}O_x$ | 314 | 74 | 88.2 |
| 8 | $Mo_{12}P_2V_1Nb_{0.5}Cs_2Cu_{0.5}Rh_{0.05}O_x$ | 314 | 74 | 88.2 |
| 9 | $Mo_{12}P_3V_1Nb_{0.5}Cs_2Cu_{0.5}Rh_{0.1}O_x$ | 326 | 46.4 | 87.2 |
| 10 | $Mo_{12}P_2V_1Cs_1Cu_{0.25}Rh_{0.2}Cr_{0.05}Fe_{0.5}O_x$ | 298 | 79.1 | 82.7 |
| 11 | $Mo_{12}P_2V_1Cs_1Cu_{0.25}Rh_{0.2}Nb_{0.2}Cr_{0.5}Fe_{0.05}O_x$ | 300 | 81.7 | 82.3 |
| 12 | $Mo_{12}P_2V_1Cs_1Cu_{0.5}Rh_{0.1}Nb_{0.5}Cr_{0.05}Fe_{0.5}Li_{0.5}O_x$ | 318 | 66.1 | 83.7 |
| 13 | $Mo_{12}P_2V_1Cs_1Cu_{0.5}Rh_{0.1}Nb_{0.5}Cr_{0.05}Fe_{0.5}Li_{0.25}Na_{0.25}O_x$ | 310 | 45.7 | 88.9 |
| 14 | $Mo_{12}P_2V_1Cs_1Cu_{0.5}Rh_{0.1}Nb_{0.5}Cr_{0.05}$ +$Fe_{0.5}Li_{0.2}$-$5Na_{0.25}O_x$ | 310 | 45.7 | 88.9 |

⁺In Example 14, 85 ml of catalyst are treated with 58.3 liters (S.T.P.) of gas/h, the composition of the gas being: 5.8% by volume of methacrolein, 5.4% by volume of $O_2$, 42.9% by volume of steam and 46.2% by volume of nitrogen.

EXAMPLE 15

To test the life of the catalysts according to the invention, a catalyst having the composition $Mo_{12}V_1P_{1.96}Nb_{0.53}Cs_{1.95}Cu_{0.5}Rh_{0.1}O_x$ is prepared by the method described in Example 14. 85 ml of the catalyst are heated to a bath temperature of 318° C., as described in Example 1B, and tested for 1,010 hours whilst keeping the bath temperature constant. The test results after various operating times are shown in Table 3 below. No decrease in conversion or in selectivity over the period of the test is observed.

TABLE 3

| Operating time hours | Conversion mole % | Yield of methacrylic acid mole % | Selectivity mole % |
|---|---|---|---|
| 96 | 74.1 | 64.5 | 87 |
| 360 | 74 | 63.4 | 85.6 |
| 720 | 74.3 | 64.9 | 87.4 |
| 1,010 | 74.2 | 63.7 | 85.9 |

We claim:
1. An oxidation catalyst wherein the catalytically active component has the general formula

$$Mo_{12}P_aRh_bCu_cV_dCs_eX_fY_gZ_hO_x,$$

where X is Cr and/or Fe, Y is Nb, Z is Na, Li, K and/or Rb, a is 0.1–4, b is 0.001–1, c is 0.05–2, d is 0.05–4, e is 0.1–5, f is 0–2, g is 0–3 and h is 0–2, and x is the number of oxygen atoms required to saturate the valencies of the other constituents.

* * * * *